US00PP13613P39

(12) United States Plant Patent
Glicenstein et al.

(10) Patent No.: US PP13,613 P3
(45) Date of Patent: Mar. 4, 2003

(54) AZALEA PLANT NAMED 'BLISS'

(75) Inventors: Leon Glicenstein, Lebanon, IN (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 186 days.

(21) Appl. No.: 09/888,800

(22) Filed: Jun. 25, 2001

(65) Prior Publication Data

US 2002/0199225 P1 Dec. 26, 2002

(51) Int. Cl.[7] ..... A01H 5/00

(52) U.S. Cl. ..... Plt./240

(58) Field of Search ..... Plt./240, 239, 238

*Primary Examiner*—Kent L. Bell
(74) *Attorney, Agent, or Firm*—C. A. Whealy

(57) ABSTRACT

A new and distinct cultivar of Azalea plant named 'Bliss', characterized by its very dark green leaves that do not abscise during the cooling and forcing periods; large plants with dense and outwardly spreading plant habit; vigorous growth habit; very freely branching habit; rapid flowering response; numerous, large and showy intense pink-colored flowers; single flower form; excellent postproduction longevity; and very low incidence of infection with Cylindrocladium in inoculated trials.

2 Drawing Sheets

BACKGROUND OF THE INVENTION

The present Invention relates to a new and distinct cultivar of Azalea, botanically known as *Rhododendron hybrida,* an evergreen greenhouse-forcing type Azalea, and hereinafter referred to by the name 'Bliss'.

The new Azalea is a product of a planned breeding program conducted by the Inventors in Salinas, Calif. and Alva, Fla. The objective of the breeding program is to create new Azalea varieties having uniform plant habit, profuse and uniform flowering, dark green foliage, good foliage retention during the cooling and forcing periods, resistance to Cylindrocladium, and excellent postproduction longevity.

The new Azalea originated from a cross made by the Inventors in December, 1991, in Salinas, Calif., of the cultivar 'Cachet', disclosed in U.S. Plant Pat. No. 6,412, as the female, or seed, parent with the cultivar 'Alaska', not patented, as the male, or pollen, parent. The new Azalea was discovered and selected by the Inventors as a flowering plant within the progeny of the stated cross in a controlled environment in Alva, Fla., in July, 1994. The selection of this plant was based on its single flower form, intense pink flower color, very large flower size, uniform flowering response, very good foliage retention, and excellent postproduction longevity.

Asexual reproduction of the new Azalea by terminal cuttings taken in a controlled environment in Alva, Fla. since April, 1995, has shown that the unique features of this new Azalea are stable and reproduced true to type in successive generations.

SUMMARY OF THE INVENTION

The new Azalea has not been observed under all possible environmental conditions. The phenotype may vary somewhat with variations in environment such as temperature, daylength, light intensity, relative humidity, fertilizer rate and type, and/or water status without, however, any variance in genotype.

The following traits have been repeatedly observed and are determined to be the unique characteristics of 'Bliss'. These characteristics in combination distinguish 'Bliss' as a new and distinct cultivar:

1. Very dark green leaves that do not abscise during the cooling and forcing periods.

2. Large plants with dense and outwardly spreading plant habit; vigorous growth habit.

3. Very freely branching habit; usually about 5 lateral branches develop after pinching.

4. Rapid flowering response; plants begin flowering about 23 days after cooling treatment.

5. Numerous, large and showy intense pink-colored flowers.

6. Single flower form.

7. Excellent postproduction longevity with plants maintaining good flower substance for about four weeks in an interior environment.

8. Very low incidence of infection with Cylindrocladium in inoculated trials.

Plants of the new Azalea differ from plants of the female parent, the cultivar 'Cachet', in the following characteristics:

1. Plants of the new Azalea are more outwardly spreading and not as compact as plants of the cultivar 'Cachet'.

2. Plants of the new Azalea have single flowers whereas plants of the cultivar 'Cachet' have double flowers.

3. Plants of the new Azalea have intense pink-colored flowers whereas plants of the cultivar 'Cachet' have fuchsia pink-colored flowers.

4. Plants of the new Azalea are more resistant to Cylindrocladium infection than plants of the cultivar 'Cachet'.

Plants of the new Azalea differ from plants of the male parent, the cultivar 'Alaska', in the following characteristics:

1. Plants of the new Azalea have single flowers whereas plants of the cultivar 'Alaska' have single to semi-double flowers.

2. Plants of the new Azalea have intense pink-colored flowers whereas plants of the cultivar 'Alaska' have white-colored flowers.

3. Plants of the new Azalea flower about 12 days earlier than plants of the cultivar 'Alaska'.

4. Plants of the new Azalea have much longer postproduction longevity than plants of the cultivar 'Alaska'.

Plants of the new Azalea can be compared to the plants of the cultivar 'YB 871 Remembrance', disclosed in U.S. Plant Pat. No. 9,132. However, in side-by-side comparisons conducted in Alva, Fla., plants of the new Azalea differed from plants of the cultivar 'YB 871 Remembrance' in the following characteristics:

1. Plants of the new Azalea are more vigorous, more outwardly spreading and not as compact as plants of the cultivar 'YB 871 Remembrance'.

2. Plants of the new Azalea have larger leaves than plants of the cultivar 'YB 871 Remembrance'.

3. Plants of the new Azalea have single flowers whereas plants of the cultivar 'YB 871 Remembrance' have semi-double flowers.

4. Plants of the new Azale have intense pink-colored flowers whereas plants of the cultivar 'YB 871 Remembrance' have dark pink-colored flowers.

5. Plants of the new Azalea have much longer postproduction longevity than plants of the cultivar 'YB 871 Remembrance'.

6. Plants of the new Azalea are more resistant to Cylindrocladium than plants of the cultivar 'YB 871 Remembrance'.

Plants of the new Azalea can be compared to the plants of the cultivar 'Party Favor', disclosed in U.S. Plant Pat. No. 10,050. However, in side-by-side comparisons conducted in Alva, Fla., plants of the new Azalea differed from plants of the cultivar 'Party Favor' in the following characteristics:

1. Plants of the new Azalea have larger flowers than plants of the cultivar 'Party Favor'.

2. Plants of the new Azalea have single flowers whereas plants of the cultivar 'Party Favor' have semi-double flowers.

3. Plants of the new Azalea have intense pink-colored flowers whereas plants of the cultivar 'Party Favor' have dark pink-colored flowers.

BRIEF DESCRIPTION OF THE PHOTOGRAPHS

The accompanying colored photographs illustrate the overall appearance of the new Azalea. These photographs show the colors as true as it is reasonably possible to obtain in colored reproductions of this type. Colors in the photographs may differ slightly from the color values cited in the detailed botanical description, which accurately describe the colors of the new Azalea.

The photograph on the first sheet comprises a side perspective view of a typical flowering plant of 'Bliss'.

The photograph on the second sheet is a close-up view of typical flowers and leaves of 'Bliss'.

DETAILED BOTANICAL DESCRIPTION

The aforementioned and following observations, measurements, values, and comparisons describe plants grown in Alva, Fla. with three plants per 15-cm containers, in a polypropylene-covered shade house during the spring under commercial production conditions. During the production of the plants, day temperatures ranged from 13 to 37° C. and night temperatures ranged from 0 to 26° C. Plants were pinched at planting, pinched a second time about 12 weeks later, and pinched a third time about 12 weeks later. After sufficient flower bud development, plants were cooled at 3 to 5° C. for four weeks to break flower bud dormancy. Plants were subsequently forced into flower under commercial production conditions in a polyethylene-covered greenhouse. Plants used for the photographs and description were about one year old.

In the following description, color references are made to The Royal Horticultural Society Colour Chart except where general terms of ordinary dictionary significance are used.

Botanical classification:

*Botanical.—Rhododendron hybrida* 'Bliss'.

*Commercial.*—Evergreen greenhouse-forcing type Azalea.

Parentage:

*Female or seed parent.—Rhododendron hybrida* cultivar 'Cachet', disclosed in U.S. Plant Pat. No. 6,412.

*Male or pollen parent.—Rhododendron hybrida* cultivar 'Alaska', not patented.

Propagation:

*Type.*—By terminal vegetative cuttings.

*Time to initiate roots.*—Summer: About 35 days at temperatures of 24° C. Winter: About 42 days at temperatures of 24° C.

*Time to develop roots.*—Summer: About 63 days at temperatures of 24° C. Winter: About 77 days at temperatures of 24° C.

*Root description.*—Fine, fibrous, freely branching, white in color.

Plant description:

*Plant form and growth habit.*—Perennial, evergreen; outwardly spreading plant habit; inverted triangle; vigorous growth habit. Densely foliated. Freely flowering; numberous flowers per plant.

*Branching habit.*—Very freely branching; about five lateral branches develop after pinching (removal of terminal apex).

*Plant height, soil level to top of flowers.*—About 25 cm.

*Plant diameter, area of spread.*—About 54 cm.

*Lateral branch description.*—Length: About 19.5 cm. Diameter at base: About 7 mm. Texture: Young: Pubescent, fine brown hairs. Mature: Woody; pubescent, fine brown hairs. Color: Young: Close to 146A. Mature: Closest to between 164A and 164B.

*Foliage description.*—Arrangement: Alternate, single. Foliage retention: Very good foliage retention on plant of the new Azalea that have been in a box for six weeks during the cooling treatment. Length: About 6.5 cm. Width: About 3.6 cm. Shape: Obovate. Apex: Cuspidate to mucronate. Base: Attenuate. Margin: Entire. Venation pattern: Pinnate. Texture, upper and lower surfaces: Leathery, tough, durable; pubescent. Luster: Upper surface: Somewhat glossy. Lower surface: Some glossiness. Color: Young and mature foliage, upper surface: Much darker green than 147A. Young and mature foliage, lower surface: Darker than 147B. Venation, upper surface: Main veins, close to 144A; lateral veins, same as lamina. Venation, lower surface: Main veins, close to 146A. to 144A; lateral veins, same as lamina. Petiole: Length: About 9 mm. Diameter:

About 3 mm. Texture: Upper surface: Smooth, glabrous. Lower surface: Pubescent. Color: Upper surface: Close to 144A. Lower surface: Close to 144A to 146A.

Flower description:

*Natural flowering season*.—Spring after sufficient cool period. If forced, plants typically flower about 23 days after a four-week cooling treatment. Flowers persistent.

*Flower arrangement*.—Flowers arranged singly at terminals with usually about two or three flowers per apex; freely flowering. Flowers face upward and outward. Slight, sweet fragrance.

*Flower appearance*.—Very large single flower form; intense pink-colored petals.

*Flower diameter*.—About 11.5 cm.

*Flower depth*.—About 7 cm.

*Postproduction longevity*.—Under interior conditions, plants maintain good flower substance for about four weeks.

*Flower bud* (*before showing color*).—Rate of opening: About three to four days depending on temperatures. Length: About 1.4 cm. Diameter: About 7.5 mm. Shape: Ovoid. Texture: Covered with fine pubescence. Color; Close to 144A to 144B.

*Petals*.—Arrangement: Single flower form; single whorl of five fused petals. Length: About 6.1 cm. Width: About 4.7 cm. Shape; Beyond fused base, roughly ovate to somewhat cordate with rounded apex. Margin: Entire. Texture, upper and lower surfaces: Smooth, satiny. Color: When opening, upper surface: Closest to 68A. When opening, lower surface: Closest to 68A. Fully opened, upper surface: Closest to 68A. Fully opened, lower surface: Slightly lighter than 68A. Throat: Closest to 68A. Spots on upper surface of lower three petals: Close to 57A.

*Sepals*.—Arrangement/appearance: Single whorl of five small sepals fused into a star-shaped calyx; leaf-like. Length: About 7.5 mm. Width: About 5 mm. Shape: Ovate to linear with acute apex. Margin: Entire. Texture, upper and lower surfaces: Pubescent. Color, upper and lower surface: 144A.

*Peduncles*.—Length: About 1.5 cm. Diameter: About 2.5 mm. Angle: Upright to 35° from vertical. Strength: Flexible; strong. Texture: Pubescent. Color: 144A.

*Reproductive organs*.—Androecium: Quantity of stamens: Five per flower. Filament length: About 4.1 cm. Filament diameter: Less than 1 mm. Filament color: 55A to 55B. Anther size: About 2.5 mm by 1 mm. Anther shape: Oblong. Anther color: Close to 64A. Amount of pollen: Scarce. Pollen color: Close to 155D. Gynoecium: Quantity of pistils: One per flower. Pistil length: About 5.4 cm. Style length: About 4.7 mm. Style diameter: Less than 1 mm. Style color: 55A to 55B. Stigma diameter: About 2 mm. Stigma shape: Rounded. Stigma color: 11D. Ovary color: 147A; heavily whiskered.

*Seed*.—Seed production has not been observed.

Weather/temperature tolerance: Plants of the new Azalea have been observed to be very tolerant to rain and wind. Plants of the new Azalea have been observed to tolerate temperatures from 0 to 37° C.

Disease resistance: In inoculated trials that were conducted in Alva, Fla. during the summers of 1997, 1999 and 2000, plants of the new Azalea have been observed to be very resistant to infection by Cylindrocladium.

It is claimed:

1. A new and distinct Azalea plant named 'Bliss', as illustrated and described.

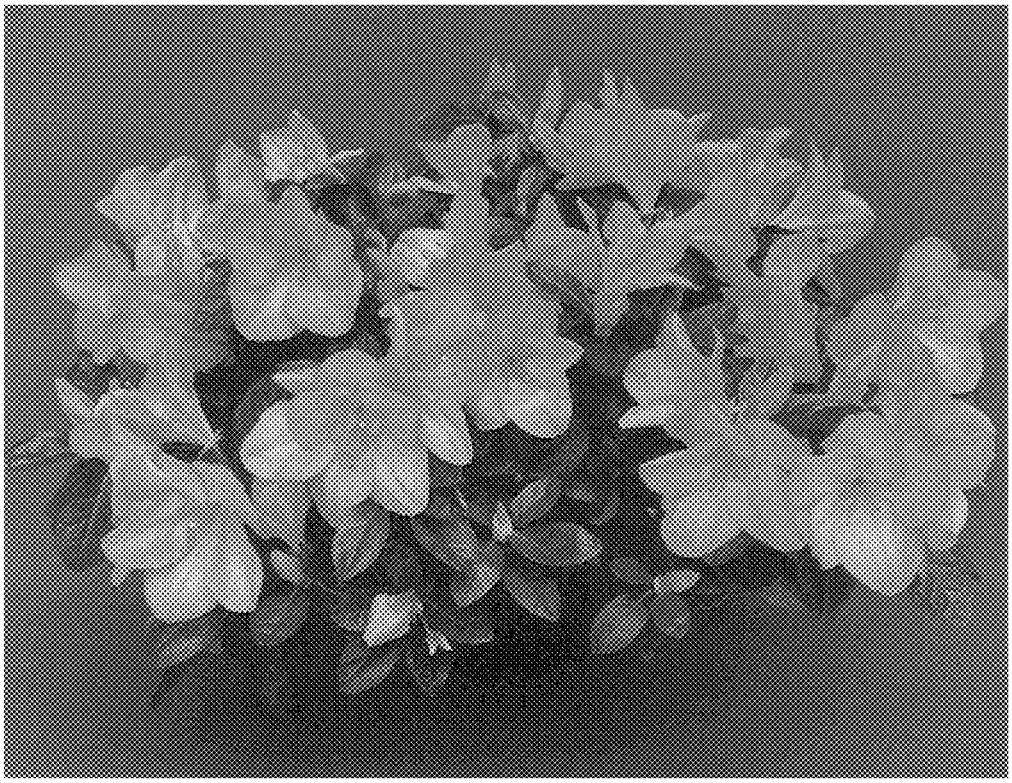

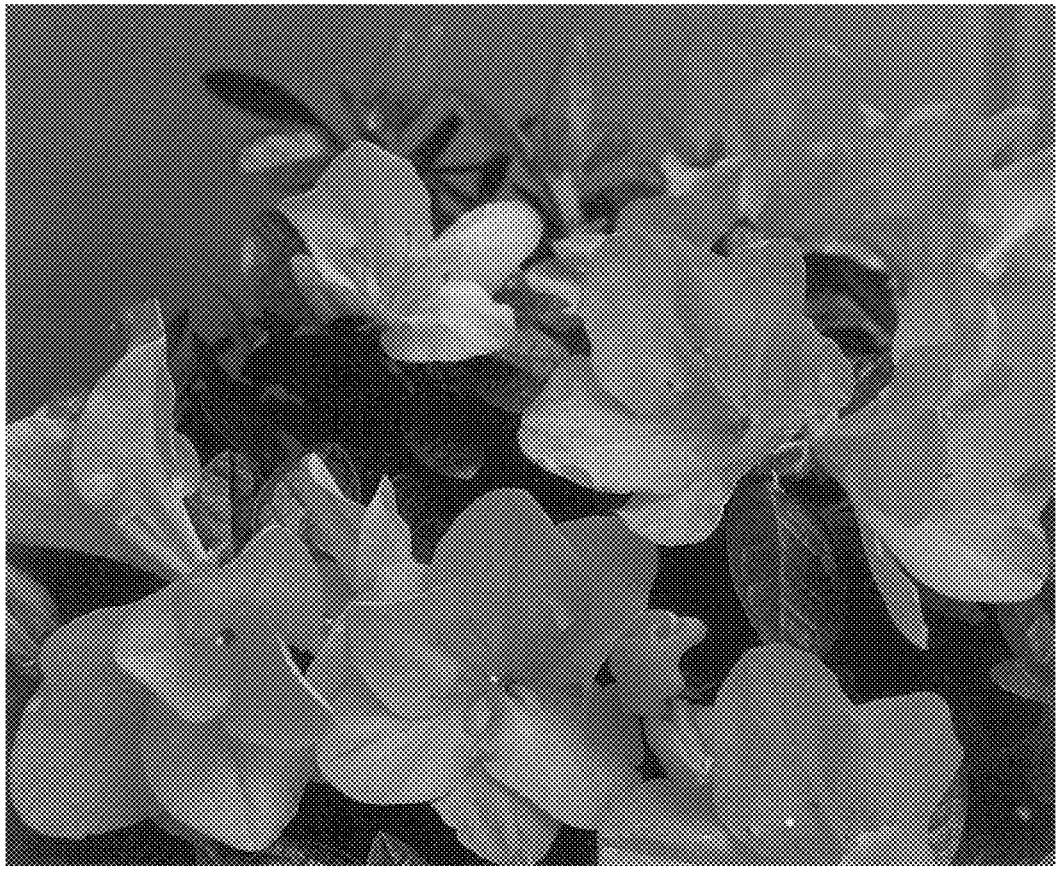

* * * * *